United States Patent [19]

Schneider

[11] 4,222,006

[45] Sep. 9, 1980

[54] THERMAL COMPOSITION CIRCUIT FOR ELECTROCHEMICAL DETECTORS

[75] Inventor: Alan A. Schneider, Reisterstown, Md.

[73] Assignee: Catalyst Research Corporation, Baltimore, Md.

[21] Appl. No.: 970,334

[22] Filed: Dec. 18, 1978

[51] Int. Cl.³ ............................................. G01N 27/42
[52] U.S. Cl. ................................. 324/441; 204/195 R
[58] Field of Search ....................... 324/441, 425, 439; 204/195 R

[56] References Cited

U.S. PATENT DOCUMENTS

| | | | |
|---|---|---|---|
| 2,828,479 | 3/1958 | Jackson, Jr. | 324/441 |
| 3,382,430 | 5/1968 | Cunniff et al. | 324/441 |
| 3,392,333 | 7/1968 | Blondfield | 324/441 |
| 3,405,048 | 10/1968 | Soltz | 324/441 |
| 3,909,386 | 9/1975 | Oswin et al. | 204/195 R |

Primary Examiner—Michael J. Tokar
Attorney, Agent, or Firm—Reed, Smith, Shaw & McClay

[57] ABSTRACT

The present invention provides a means for compensating for temperature induced variations in the span and zero signals of an electrochemical detector. The invention comprises a first compensating circuit electrically connected to the output of the detector and includes a first thermistor and a first amplifier which compensate for all variations in the span signal as well as some variation in the zero signal. A second compensating circuit comprising a second thermistor and a power source and voltage divider network electrically connected to the second thermistor for adjusting zero current wherein the output of the second thermistor is algebraically added to the output of the first compensating circuit by a second amplifier connected to the outputs of the first and second circuit and includes a resistance feedback loop to the output of the second thermistor.

5 Claims, 3 Drawing Figures

THERMAL COMPOSITION CIRCUIT FOR ELECTROCHEMICAL DETECTORS

FIELD OF THE INVENTION

The present invention relates to a thermal compensating circuit, and, in particular, to a circuit for compensating variations due to temperature in both zero and span signals of electrochemical detectors.

BACKGROUND OF THE INVENTION

Electrochemical detectors are devices which measure selected gases, such as CO, $CO_2$, and $H_2$, $CH_4$ and the like. These devices are particularly useful in measuring very small amounts of the selected gas such as for example, 2 to 10 parts per million, and must be accurate particularly were the threshhold limit value of a regulated substance is being measured.

Typically, electrochemical devices have a zero signal which is defined as a signal produced by the detector when the selected gas is not present in the cell and a span signal which is the signal produced by the detector when the selected gas is present. Numerous electrical circuits are available to convert span signals from the electrochemical cell into useful information either by a meter or recording device. Circuits for adjusting the zero and span signals are also known.

In addition to the conventional adjustment or calibration requirements, both the zero and span signals may be temperature dependent. Accordingly, it is necessary to compensate for any such temperature induced variation within the expected working range of the cell. One such compensating circuit is disclosed in U.S. Pat. No. 3,909,386. As described in that patent, the variations due to temperature in both span and zero signals are logarithmic functions rather than linear functions. The circuit described therein utilizes a thermistor designed to compensate for the span signal variations and a thermistor circuit designed to compensate for the zero signal variations. The two thermistors, however, do not mutually interact.

While it has been generally known that the changes in span and zero signals are not uniform, it has been found that the variation in zero current is normally much greater than that of the span signal. Moreover, it has been found that the variation due to temperature in zero current is normally greater than that which can be compensated with commercially available thermistors. Therefore, compensating circuits similar to that disclosed in U.S. Pat. No. 3,909,386 do not provide adequate compensation, particularly with respect to zero signal variations.

It is, therefore, an object of the present invention to provide a thermal compensating circuit which will adequately compensate for both variations in the span and zero signals. It is a further object of the present invention to provide a thermal compensation circuit which will adequately compensate the larger variation normally found to exist in zero signals of electrochemical detectors and to overcome the disadvantages inherent in those circuits utilizing thermistors that do not mutually interact.

SUMMARY OF THE INVENTION

Generally, electrochemical detectors include an electrochemical cell which includes in addition to an electrolyte, a reference electrode, a counter electrode, and a working electrode. In such cells, the current flows through the counter electrode to maintain a fixed potential at the working electrode. While the reference electrode in theory should not have a current flow, the difference in potential between it and the working electrode is affected by the electrochemical activity at the working electrode. The cell current flow is between the working electrode and the counter electrode and the potential of the working electrode is measured with respect to the reference electrode. In a two-electrode configuration, the current signal due to electrochemical activity at the working electrode is measured with a fixed voltage between the two electrodes. Normally, the electrode potential of the working electrode is less stable in the two-electrode configuration than in the three-electrode and includes more chance of error due to iR drop in the cell as well as possible internal polarization affects. The present invention, however, is applicable to both types of electrochemical detectors.

The compensating circuit of the present invention includes a first compensating circuit having a first thermistor and a first amplifier which is electrically connected to the output of the working electrode of the detector. The first compensating circuit may additionally include resistors, either in series or parallel to the thermistor. The first circuit compensates for variations in span signal as well as for some variation induced in the zero signal. A second compensating circuit comprises a second thermistor electrically connected to a power source and voltage divider network for adjusting zero current. The output of the second thermistor is electrically connected to the output of the first conduit and its signal is algebraically added to the signal output from the first compensating circuit by a second amplifier. Electrically connected to the output of the second amplifier is a resistor feedback loop connected to the output of the second thermistor as well as resistors for limiting current output of the second amplifier.

Under normal operating conditions, the compensation provided by the second thermistor adds, algebraically, the compensation not provided to the zero current by the first compensating circuit. The two circuits together will provide adequate compensation not only to variation in span, but also in the zero signal. Other advantages of the present invention will become apparent from a perusal of the following detailed description of the presently preferred embodiment taken in connection with the drawings.

DESCRIPTION OF THE BEST MODE CONTEMPLATED

Figure 1:
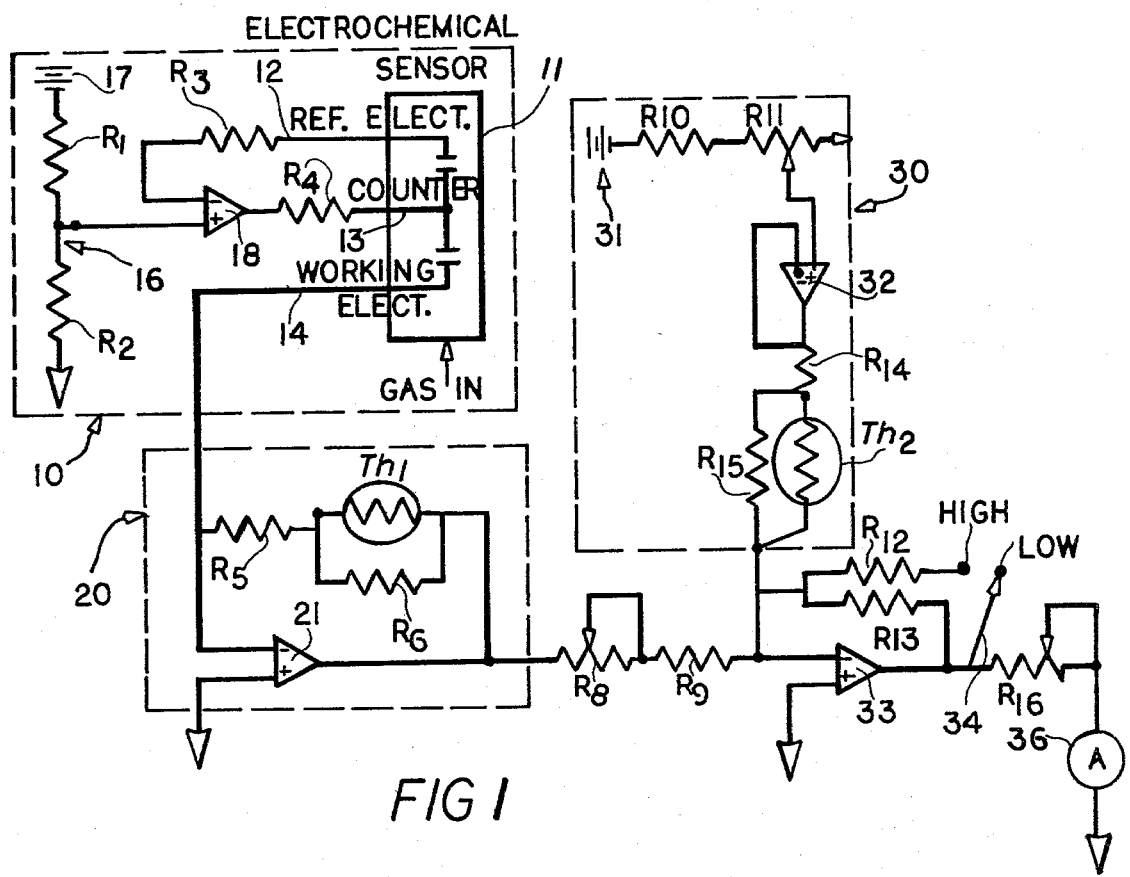
FIG. 1 is a schematic diagram of the present invention.

With reference to FIG. 1, a potentiostatic sensor circuit 10 is shown which includes electrochemical sensing cell 11 designed in a manner well known to the art to detect a selected gas. Although a three-electrode cell is shown, the present invention is equally applicable to two-electrode cells.

Cell 11 includes a reference electrode 12, a counter electrode 13 and a working electrode 14. In conventional cells, the working electrode is positioned adjacent to the gas input opening and reference electrode 12, typically an air electrode, is positioned in the electrolyte sufficiently away from the gas to avoid the electrochemical effects thereof.

Potentiostatic circuit 10 includes a divider network 16 consisting of resistors $R_1$ and $R_2$ which is electrically connected to a power source 17. Divider network 16 supplies reference voltage to the non-inverting input of operational amplifier 18. Operational amplifier 18 together with resistors $R_3$ and $R_4$ are designed to maintain a zero potential difference between reference electrode 12 and divider network 16. Operational amplifier 18 senses any small differences between the voltage of electrode 12 and the reference voltage of network 16 and causes sufficient current to flow between the counter electrode 13 and the working electrode 14 to bring that difference to zero.

The current from working electrode flows to first compensating circuit 20. This circuit not only provides thermal compensation but also maintains the voltage $V_1$ of the working electrode at mutual ground.

First compensating circuit 20 comprises first amplifier 21, resistors $R_5$ and $R_6$ and first thermistor $Th_1$. First compensating circuit 20 is a modified current-to-voltage converter. The output signal amplifier 21 is proportional to the sum of the zero and span currents which have been thermally compensated by thermistor $Th_1$ and resistors $R_5$ and $R_6$. Resistors $R_5$ and $R_6$ together with thermistor $Th_1$ are selected to take care of the span current variations (which is defined by the slope of line $E_s$ of FIG. 3).

Figure 2:
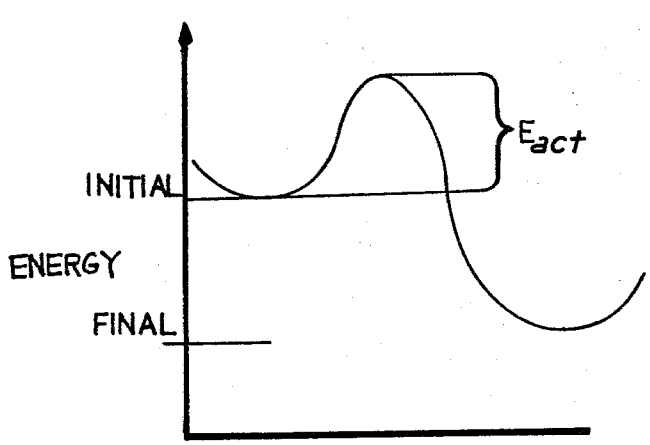
FIG. 2 is a graphic representation of activation energy.

Span current $i_s$ is defined as the current due to the electrochemical reaction of the selected gas at the working electrode. It obeys the general equation $$i_s = A_s e^{-\Delta E_s/RT}$$

where $E_s$ is the energy of activation of the electrochemical reaction due to the presence of the selected gas, $A_s$ is a preexponential constant, R is the universal gas constant and T is the absolute temperature. The activation energy, whether span or zero signal, is the energy barrier which the reactant species must overcome in passing from the initial state to the final state the electrochemical reaction. The energy during the reaction are represented pictorially in FIG. 2 showing the activation barrier, E act. In most electrochemical cells the energy of activation of zero current is greater than that of span current.

Figure 3:
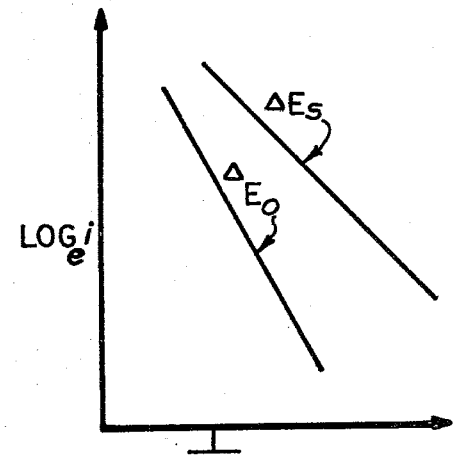
FIG. 3 is a graphical representation of the logarithmic variation of span and zero signal due to temperature.

FIG. 3 is a plot of current, $\log_e i$, against the reciprocal of temperature. The slope of the curves represent the energy of activation ($\Delta E_s$) of span current ($i_s$) and the energy of activation ($\Delta E_o$) of zero current ($i_o$). The current of working electrode 14 is equal to $i_o + i_s = A_o e^{-\Delta E_o/RT} + A_s e^{-\Delta E_s/RT}$ Resistance, $R_T$, of the thermistors is: $R_T = R_o e^{+\Delta E_g/RT}$, where $R_o$ is a pre-exponential factor and $E_g$ is the band gap energy. The resistances of $T_1$, $R_5$ and $R_6$ are selected to compensate for all of the variations in span current as well as a part of the zero current variation. Normally, however, additional compensation is required for the variations to zero current. Accordingly, a second compensating circuit 30 is provided.

Second compensating circuit 30 comprises a voltage source consisting of power source 31 and resistors $R_{10}$ and $R_{11}$. Resistor $R_{11}$ is preferably a variable resistor which is used to adjust the zero current of the detector circuit. As with conventional currents, the zero adjustment is made when no gas is present. Operational amplifier 32 is a high input-impedance voltage follower used to buffer the voltage from the divider network $R_{10}$ and $R_{11}$. The current flowing from network 30 is a function of the voltage at the top of $R_{11}$ and the resistance of the compensation network comprising second thermistor $Th_2$ and resistors $R_{14}$ and $R_{15}$. The values of $Th_2$ and resistors $R_{14}$ and $R_{15}$ are selected to compensate for the variation in zero current not compensated by first compensation circuit 20.

A better understanding of the differences between this invention and that of the prior art may be seen by simplifying the circuit of FIG. 1 somewhat. If both thermistors are identical and if $R_5$ and $R_{14}$ are very much smaller than the resistances of $Th_1$ and $Th_2$ and $R_6$ and $R_{15}$ are very much larger, then the zero current compensation provided by circuits 20 and 30 is given by the simple expression $$[R_o e^{\Delta E_g/RT}] \cdot [R_o e^{\Delta E_g/RT}] = R_o e^{2\Delta E_g/RT}$$

This is to be compared to the compensation provided by prior art circuits which would be given by $$[R_o e^{\Delta E_g/RT}] + [R_o e^{\Delta E_g/RT}] = 2R_o e^{\Delta E_g/RT}$$

With prior art circuits, the relationship is additive rather than multiplicative because the thermistors do not mutually interact. The present invention can provide up to twice the compensation per degree of temperature change when compared to prior art circuits because thermal compensation depends on the exponential factor and not the pre-exponential factor.

A similar comparison between this invention and prior art circuits can be made if $R_5$, $R_{14}$, $R_6$ and $R_{15}$ are not the extreme values given in the above example; the mathematics, however, is more complex. The multiplicative effect of the mutual interaction of circuits 20 and 30 is still valid for any values of $R_5$, $R_{14}$, $R_6$ and $R_{15}$ and can still be compared to the additive effect of prior art circuits.

The choice of $R_5$ and $R_6$ is based on the value of the span current activation energy ($\Delta E_s$) and the $\Delta E_g$ value of $Th_1$. $R_5$ and $R_{14}$ can be chosen such that the resistance of the network comprising $R_5$, $R_6$ and $Th_1$, when plotted as log (R) verses 1/T, is essentially linear (within a few percent) over the range of operating temperatures of the gas sensing instrument (e.g. 0° C. to 40° C.) and has a slope equal in magnitude to $\Delta E_s$. That is, the network acts as if it were a single thermistor with a gap energy $\Delta E_1 \leq \Delta E_g$ where $\Delta E_1$ is equal in magnitude to $\Delta E_s$. It compensates fully the variation in span current with temperature and also compensates partially the variation of zero current with temperature.

The choice of $R_{14}$ and $R_{15}$ is based on the values of the zero current activation energy $\Delta E_o$, the $\Delta E_g$ value of $Th_2$ and also $\Delta E_1$. $R_{14}$ and $R_{15}$ are chosen such that the resistance of the network comprising $R_{14}$, $R_{15}$ and $Th_2$, when plotted as log (R) verses 1/T, is essentially linear over the range of operating temperatures and has a slope $\Delta E_2$ equal in magnitude to $\Delta E_o - \Delta E_1$ and less than or equal to the $\Delta E_g$ value of $Th_2$. The compensation of zero current provided by both networks 20 and 30, by their mutual interaction, is proportional to $[1^{\Delta E_1/RT}] \cdot [1^{(\Delta E_o - \Delta E_1)/RT}] = 1^{\Delta E_o/RT}$ which is the desired result. It should be noted that the second compensation circuit alone provided not the full compensation $1^{\Delta E_o/RT}$ but only a fraction $1^{(\Delta E_o - \Delta E_1)/RT}$. As was stated above, it is often impossible to provide a commercially available thermistor with an $E_g$ of $\Delta E_o$, but thermistor with an $E_g = (\Delta E_o - \Delta E_1)$ can normally be obtained.

Resistors $R_8$ and $R_9$ are preferably included to limit the current from the first compensating circuit 20. As shown $R_8$ is a variable resistor which is useful in making rough circuit adjustments to compensate for variations between different electrochemical cells 11 as well as to extend the useful life of the detector.

Switch 34 including resistors $R_{12}$ and $R_{13}$ is preferably included to provide a dual range for the detector. Variable resistor $R_{16}$ is provided to calibrate or adjust the span current which is measured by ammeter 36. Ammeter 36 is typically calibrated to indicate the concentration of the selected gas. With switch 34 and resistors $R_{12}$ and $R_{13}$, ammeter 36 is shown to have two ranges, such as for example 0 to 2 ppm and 1 to 10 ppm. In such case resistor $R_{13}$ would be four times the value of resistor $R_{12}$.

While the best mode for practicing the invention has been described in particularity, it should be clear to those skilled in the art that the invention may be otherwise embodied. In particular those circuits functioning as current-to-voltage converts can be designed as voltage-to-current circuits where required for specific electrochemical cells. Also, any or all of resistors $R_5$, $R_6$, $R_{14}$ and $R_{15}$ may not be necessary. As should be clear, the inventive features are defined in the appended claims.

What is claimed is:

1. Means for compensating for variations resulting from temperature in span and zero signals of electrochemical detectors comprising:
   a. a first compensating circuit electrically connected to the output of said detector and including a first thermistor and a first operational amplifier the output of which provides a first signal that compensates for all variations in span and at least a portion of any variation in the zero signal;
   b. a second compensating circuit comprising a second thermistor, a divider network including a power source for adjusting the zero signal and providing an input signal to said second thermistor, said second circuit providing a second thermally compensating signal based upon variations in the zero signal; and
   c. a second amplifier means having an input consisting of said first and second signal and at least one resistive feedback loop for algebraically adding the first and second signals.

2. Thermal compensating means as set forth in claim 1 wherein said first compensating circuit includes at least one resistor.

3. Thermal compensating means as set forth in claim 1 wherein said second compensating circuit includes at least on resistor.

4. Thermal compensating means as set forth in claim 1 wherein the outputs of the first and second compensating circuits are electrically connected through a variable resistor.

5. Thermal compensating means as set forth in claim 1 wherein the electrochemical detector is potentiostated.

* * * * *

UNITED STATES PATENT OFFICE
CERTIFICATE OF CORRECTION

PATENT NO. : 4,222,006
DATED : September 9, 1980
INVENTOR(S) : Alan A. Schneider It is certified that error appears in the above-identified patent and that said Letters Patent are hereby corrected as shown below:

On the front page, in the title [54], after "THERMAL" delete "COMPOSITION" and substitute therefor -- COMPENSATION --;

Column 1, line 1, after "THERMAL" delete "COMPOSITION" and substitute therefor -- COMPENSATION --;

Column 2, line 31, after "first" delete "conduit" and substitute therefor -- circuit --;

Column 4, line 64, the equation should read $\left[\varrho^{\Delta E1/RT}\right] \cdot \left[\varrho^{(\Delta Eo-\Delta E1)/RT}\right] = \varrho^{\Delta Eo/RT}$ ;

Column 4, line 67, the equation should read $\varrho^{\Delta Eo/RT}$ ;

Column 4, line 67, after "fraction" delete the equation "$1^{(\Delta Eo-\Delta E1)/RT}$" and substitute therefor -- $\varrho^{(\Delta Eo-\Delta E1)/RT}$ --;

Column 6, line 26, after "least" delete "on" and substitute therefor -- one --.

Signed and Sealed this

Ninth Day of December 1980

[SEAL]

Attest:

SIDNEY A. DIAMOND

Attesting Officer     Commissioner of Patents and Trademarks